(12) United States Patent
Losada et al.

(10) Patent No.: US 8,524,171 B2
(45) Date of Patent: *Sep. 3, 2013

(54) DEVICE FOR SEPARATING COMPONENTS OF A FLUID SAMPLE (75) Inventors: Robert J. Losada, Astoria, NY (US); Gregory L. Lusardi, Hackettstown, NJ (US); Fu-Chung Lin, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/085,831

(22) Filed: Apr. 13, 2011

(65) Prior Publication Data

US 2011/0187021 A1 Aug. 4, 2011

Related U.S. Application Data

(60) Division of application No. 10/785,893, filed on Feb. 24, 2004, now Pat. No. 7,947,236, and a continuation-in-part of application No. 09/727,282, filed on Nov. 30, 2000, now Pat. No. 6,803,022, and a continuation-in-part of application No. 09/454,988, filed on Dec. 3, 1999, now Pat. No. 6,479,298.

(51) Int. Cl.
*B01D 21/00* (2006.01)

(52) U.S. Cl.
USPC .................................................. 422/527

(58) Field of Classification Search
USPC .................................................. 422/527
See application file for complete search history.

(56) References Cited

U.S. PATENT DOCUMENTS

| | | | |
|---|---|---|---|
| 3,779,383 A | 12/1973 | Ayres | |
| 3,882,021 A | 5/1975 | Ayres | |
| 3,887,464 A | 6/1975 | Ayres | |
| 3,887,466 A | 6/1975 | Ayres | |
| 3,890,237 A | 6/1975 | Welch | |
| 3,891,553 A | 6/1975 | Ayres | |
| 3,894,950 A | 7/1975 | Ayres et al. | |
| 3,897,343 A | 7/1975 | Ayres | |
| 3,909,419 A | 9/1975 | Ayres | |
| 3,919,085 A * | 11/1975 | Ayres | 210/774 |
| 3,929,646 A | 12/1975 | Adler | |
| 3,957,654 A | 5/1976 | Ayres | |
| 3,972,812 A | 8/1976 | Gresl, Jr. | |
| 4,088,582 A | 5/1978 | Murty et al. | |
| 4,134,832 A | 1/1979 | Heimreid | |
| 4,152,270 A | 5/1979 | Cornell | |
| 4,294,707 A | 10/1981 | Ikeda et al. | |
| 4,315,892 A | 2/1982 | Stone et al. | |
| 4,417,981 A | 11/1983 | Nugent | |
| 4,443,345 A | 4/1984 | Wells | |

(Continued)

FOREIGN PATENT DOCUMENTS

| | | |
|---|---|---|
| EP | 1106253 A2 | 6/2001 |
| JP | 49047973 A | 5/1974 |

(Continued)

*Primary Examiner* — Lore Jarrett
(74) *Attorney, Agent, or Firm* — The Webb Law Firm (57) ABSTRACT

A device for separating heavier and lighter fractions of a fluid sample is provided, the device including a container and a unitary separator located therein, the separator having an overall density between the heavier and light fractions. The separator is capable of moving between the fractions upon centrifugation, and sealing the fractions from one another when centrifugation ends.

9 Claims, 9 Drawing Sheets

(56) References Cited

U.S. PATENT DOCUMENTS

| | | |
|---|---|---|
| 4,770,779 A | 9/1988 | Ichikawa et al. |
| 4,853,137 A | 8/1989 | Ersson |
| 5,271,852 A | 12/1993 | Luoma, II |
| 5,454,958 A | 10/1995 | Fiehler |
| 5,455,009 A | 10/1995 | Vogler et al. |
| 5,632,905 A | 5/1997 | Haynes |
| 5,785,925 A | 7/1998 | U'Ren |
| 6,063,297 A | 5/2000 | Antanavich et al. |
| 6,465,256 B1 | 10/2002 | Iskra |
| 6,479,298 B1 | 11/2002 | Miller et al. |
| 6,497,325 B1 | 12/2002 | DiCesare et al. |
| 6,516,953 B1 | 2/2003 | DiCesare et al. |
| 6,793,892 B1 | 9/2004 | Niermann |
| 6,803,022 B2 | 10/2004 | DiCesare et al. |
| 7,153,477 B2 | 12/2006 | DiCesare et al. |

FOREIGN PATENT DOCUMENTS

| | | |
|---|---|---|
| JP | 56118669 A | 9/1981 |
| JP | 59020856 A | 2/1984 |
| JP | 11314011 | 11/1999 |
| JP | 2000189407 | 7/2000 |
| JP | 2000199760 | 7/2000 |

* cited by examiner

DEVICE FOR SEPARATING COMPONENTS OF A FLUID SAMPLE

CROSS REFERENCE TO RELATED APPLICATIONS

The present application is a divisional of, and claims priority to, U.S. patent application Ser. No. 10/785,893 filed Feb. 24, 2004, entitled "Device for Separating Components of a Fluid Sample", which is a continuation-in-part of U.S. patent application Ser. No. 09/727,282 filed Nov. 30, 2000, now U.S. Pat. No. 6,803,022, which is a continuation-in-part of U.S. patent application Ser. No. 09/454,988 filed Dec. 3, 1999, now U.S. Pat. No. 6,479,298, the entire disclosures of each of which are hereby incorporated by reference.

BACKGROUND OF THE INVENTION

1. Field of the Invention

This invention relates to a device for separating heavier and lighter fractions of a fluid sample, and in particular a container containing a separator that provides such separation of blood upon centrifugation.

2. Description of Related Art

Diagnostic tests may require separation of a patient's whole blood sample into components such as serum or plasma (a lighter phase component) and red blood cells (a heavier phase component). Samples of whole blood are typically collected by venipuncture through a cannula or needle attached to a syringe or an evacuated collection tube. Separation of the blood into serum or plasma and red blood cells is then accomplished by rotation of the syringe or tube in a centrifuge. The tube or syringe generally contains a barrier that moves between the two phases upon centrifugation, and maintains that separation thereafter to allow subsequent examination of the individual components.

A variety of devices have been used in collection devices to divide the area between the heavier and lighter phases of a fluid sample. The most widely used devices include thixotropic gel materials such as polyester gels in a tube. These devices require special manufacturing equipment to prepare the gel and to fill the tubes. Moreover, the shelf-life of the product may be limited because over time, globules of gel may be released from the gel mass. These globules may enter the serum sample gel and may be released from the gel mass. These globules may enter the serum sample and thereby clog the measuring instruments. Such clogging can lead to considerable downtime for an instrument. In addition, no commercially available gel is completely chemically inert to all analytes. If certain drugs are present in the blood sample when it is taken, there can be an adverse chemical reaction with the gel.

Therefore, a need exists for a separator device that avoids the problems of gels. Such a device advantageously exhibits one or more of the following properties: (i) easily used to separate a blood sample; (ii) largely unaffected by temperature during storage and shipping; (iii) stable to radiation sterilization; (iv) employs the benefits of a thixotropic gel barrier yet avoids the disadvantages of placing a gel in contact with the separated blood components; (v) reduces cross contamination of the heavier and lighter phases of the sample during centrifugation; (vi) reduces adhesion of the lower and higher density materials against the separator device; (vii) able to move into position to form a barrier in less time than conventional methods and devices; (viii) able to provide a clearer specimen with less cell contamination than conventional methods and devices; and (ix) able to be used with standard sampling equipment.

SUMMARY OF THE INVENTION

The invention relates to an assembly for separating a fluid sample into a higher density phase and a lower density phase. Typically, the assembly comprises a container such as a tube and a separator located in the tube.

A typical tube comprises an open end, a closed end, and a sidewall extending between the open end and closed end. The sidewall comprises an outer surface and an inner surface. The tube further comprises a closure disposed to fit in the open end of the tube, typically with a resealable septum. Alternatively, both ends of the tube may be open, and both ends of the tube may be sealed by elastomeric closures. At least one of the closures of the tube may include a needle pierceable resealable septum.

The separator element comprises an overall density at a target density of $\sigma_t$. The target density is required to separate a fluid sample into at least two phases. The separator comprises at least two or more regions of differing densities. Typically, at least one of the regions is higher than the target density and at least one of the regions is lower than the target density.

In one embodiment, the separator includes opposed top and bottom ends and comprises a bellows, a ballast, and a float. The separator is disposed in the tube at a location between the top closure and the bottom of the tube. The components of the separator are dimensioned and configured to achieve an overall density for the separator that lies between the densities of the phases of a fluid sample, such as a blood sample.

The bellows of the separator is molded from a resiliently deformable material that exhibits good sealing characteristics when placed against an adjacent surface. The bellows has an upper end that is at or in proximity to the top end of the separator and an opposed lower end that is disposed between the opposed ends of the separator.

The upper end of the bellows may be formed from a material that may be pierced by a needle cannula for depositing a fluid sample into the tube. Additionally, the upper end of the bellows initially may be engaged releasably with the closure mounted in the open top end of the tube.

Preferably, the bellows includes a toroidal sealing section which, in an unbiased state of the bellows, defines an outer diameter that exceeds the inside diameter of the tube. However, the bellows can be deformed slightly so that the outer circumferential surface of the toroidal sealing section is biased against the inner circumferential surface of the tube to achieve a sealing engagement between the bellows and the tube. The bellows may be elongated by oppositely directed forces in proximity to the opposed upper and lower ends thereof. Elongation of the bellows in response to such oppositely directed forces will reduce the outside diameter of the toroidal sealing section of the bellows. Sufficient elongation of the bellows will cause the toroidal sealing section of the bellows to be spaced inwardly from the internal surface of the blood collection tube, and thereby allow the separator to move within the tube.

Desirably, the toroidal sealing section may be comprised of any natural or synthetic elastomer or mixture thereof, that is inert to the fluid sample of interest and is flexible.

In use, a fluid sample enters the assembly by needle. Where the separator is secured at the top of the tube, the needle pierces a portion of the bellows adjacent the top end of the separator and partially through the hollow interior of the float.

The needle is withdrawn from the assembly and the septum of the closure and the bellows reseals.

The assembly is then subjected to centrifugation. Forces exerted by the centrifuge causes a gradual separation of the phases of the fluid sample such that the more dense phase moves toward the bottom end of the tube, and the less dense phase is displaced to regions of the tube above the more dense phase. Simultaneously, the centrifugal load will cause the dense ballast to move outwardly relative to the axis of rotation and toward the bottom of the tube. This movement of the ballast will generate an elongation and narrowing of the bellows. Thus, the outside diameter of the toroidal sealing section of the bellows will become less than the inside diameter of the tube. Additionally, the centrifugal load and the deformation of the bellows will cause the separator to disengage from the top closure. Hence, the separator will begin to move toward the bottom of the tube. Air trapped between the fluid sample and the separator initially will move through the circumferential space between the separator and the tube. After sufficient movement, the bottom end of the separator will contact the surface of the fluid sample. At this point, air trapped within the hollow interior of the separator can impede further downward movement of the separator into the fluid sample. However, this air can pass through the defect in the bellows caused by the needle or through some other manufactured defect in the bellows.

The ballast will cause the separator to sink into the fluid sample while the float will buoyantly remain near the surface of the fluid sample thereby causing an elongation and narrowing of the bellows. The less dense liquid phase of the fluid sample will move through the space between the separator and the walls of the tube. As noted above, the overall density of the separator is selected to be less than the density of the formed phase of the fluid sample, but greater than the density of the less dense liquid phase of the fluid sample. Thus, the separator will stabilize at a location between the formed and liquid phases of the fluid sample after a sufficient period of centrifugation. The centrifuge then is stopped. The termination of the centrifugal load enables the toroidal sealing section of the bellows to return toward its unbiased dimensions, and into sealing engagement with the interior of the tube. The less dense liquid phase of the fluid sample can be separated from the tube by either removing the closure or passing a needle through the closure. Alternatively, in certain embodiments, the more dense formed phase can be accessed through a sealed opening in the bottom end of the tube.

In another embodiment, it is possible for the separator element to be a unitary structure having regions of different densities that provide, for example, the functionality of the buoyancy member and ballast member discussed herein. (Unitary indicates a single mechanical component versus a combination of mechanical components, with the single mechanical component made up of one or more materials.) For example, it is possible for the separator element to be a sphere-like element formed from a polymeric material, where the upper region of the element comprises a relatively low density material, and the lower region contains a relatively high density material. (The separator may have a density gradient, such that distinct regions of uniform density may not exist, but portions of the separator will have different average densities.) Upon centrifugation, the low and high density regions would act as the buoyancy and ballast members, respectively, with at least a portion of the region therebetween acting as a sealing member.

It is possible to obtain the high and low density regions by a variety of techniques, including molding a high density elastomeric matrix with low density components, including air bubbles or voids, distributed at an upper region therein (to provide buoyancy), or to mold a low density elastomeric matrix with high density components distributed at a lower region therein (to provide ballast). It is also possible to co-mold two or more different materials (or the same materials but having different densities) to provide the distinct densities.

The assembly of the invention is advantageous over existing separation products that use gel. For example, the separator of the invention will not interfere with analytes as compared to gels that may do so, nor will the separator of the invention interfere with therapeutic drug monitoring analytes. Other advantages that the separator may provide over gel include reduced separation time, avoidance of gel residuals, no interference with instrument probes, more acceptable blood banking tests, and a cleaner sample (where the blood is initially provided beneath the separator) due to the fact that only the cell-free fraction contacts the upper portion of the separator.

DETAILED DESCRIPTION

In one embodiment, the separator includes opposed top and bottom ends and comprises a bellows, a ballast, and a float. The separator is disposed in the tube at a location between the top closure and the bottom of the tube. The components of the separator are dimensioned and configured to achieve an overall density for the separator that lies between the densities of the phases of a fluid sample, such as a blood sample.

The bellows of the separator is molded from a resiliently deformable material that exhibits good sealing characteristics when placed against an adjacent surface. The bellows has an upper end that is at or in proximity to the top end of the separator, and an opposed lower end that is disposed between the opposed ends of the separator.

The upper end of the bellows may be formed from a material that may be pierced by a needle cannula for depositing a fluid sample into the tube. Additionally, the upper end of the bellows initially may be engaged releasably with the closure mounted in the open top end of the tube.

Preferably, the bellows includes a toroidal sealing section which, in an unbiased state of the bellows, defines an outer diameter that exceeds the inside diameter of the tube. However, the bellows can be deformed slightly so that the outer circumferential surface of the toroidal sealing section is biased against the inner circumferential surface of the tube to achieve a sealing engagement between the bellows and the tube. The bellows may be elongated by oppositely directed forces in proximity to the opposed upper and lower ends thereof. Elongation of the bellows in response to such oppositely directed forces will reduce the outside diameter of the toroidal sealing section of the bellows. Sufficient elongation of the bellows will cause the toroidal sealing section of the bellows to be spaced inwardly from the internal surface of the blood collection tube.

Desirably, the toroidal sealing section may be comprised of any natural or synthetic elastomer or mixture thereof, that is inert to the fluid sample of interest and is flexible.

Preferably, the toroidal sealing section comprises a qualitative stiffness, expressed as follows:

$$S^* = K/(a\rho_w D^2)$$

whereby "$S^*$" is the non-dimensional stiffness coefficient, "k" is a force required to deflect the bellows a given length, "a" is the applied acceleration, "D" is the diameter of the toroidal sealing section, and "$\rho_w$" is the density of water.

Desirably, the qualitative stiffness of the toroidal sealing section is from about 0.00006 to about 190.

Preferably, the toroidal sealing section may be subjected to a characteristic or radial deflection under an applied load such as an axially applied load. The characteristic or radial deflection is defined as a change in length of the toroidal sealing section relative to the change in cross section diameter of the toroidal sealing section. Preferably, the toroidal sealing section has a characteristic or radial deflection ratio of about 1.5 to about 3.5.

Preferably, the toroidal sealing section when subjected to an applied load, such as centrifugation, to cause axial deformation of the toroidal sealing section, the change in cross section diameter of the toroidal sealing section may be expressed as follows:

$$((D_{before} - D_{during})/D_{before}) \times 100\% = \Delta D_m$$

wherein "$\Delta D_m$" is from about 5% to about 20%.

Therefore, a change in cross section diameter of the toroidal sealing section is proportional to the undeflected cross section diameter of the toroidal sealing section. Preferably, the proportion is from about 0.03 to about 0.20.

In this embodiment, the ballast is a substantially tubular structure formed from a material having a greater density than the heavy phase of blood. The generally tubular ballast has a maximum outside diameter that is less than the inside diameter of the tube. Hence, the ballast can be disposed concentrically within and spaced from a cylindrical sidewall of the tube. The ballast may be securely and permanently mounted to the lower end of the bellows.

In this embodiment, the float is formed from a material having a density less than the density of the lighter phase of the blood and may be engaged near the upper end of the bellows. Additionally, the float is movable relative to the ballast. For example, the float may be substantially tubular and may be slidably telescoped concentrically within the tubular ballast. Hence, the float and the ballast can move in opposite respective directions within the tube.

In use, a fluid sample enters the assembly by needle. Where the separator is secured at the top of the tube, the needle pierces a portion of the bellows adjacent the top end of the separator and partially through the hollow interior of the float. The needle is withdrawn from the assembly and the septum of the closure and the bellows reseals.

The assembly is then subjected to centrifugation. Forces exerted by the centrifuge causes a gradual separation of the phases of the fluid sample such that the more dense phase moves toward the bottom end of the tube, and the less dense liquid is displaced to regions of the tube above the more dense phase. Simultaneously, the centrifugal load will cause the dense ballast to move outwardly relative to the axis of rotation and toward the bottom of the tube. This movement of the ballast will generate an elongation and narrowing of the bellows. Thus, the outside diameter of the toroidal sealing section of the bellows will become less than the inside diameter of the tube. Additionally, the centrifugal load and the deformation of the bellows will cause the separator to disengage from the top closure. Hence, the separator will begin to move toward the bottom of the tube. Air trapped between the fluid sample and the separator initially will move through the circumferential space between the separator and the tube. After sufficient movement, the bottom end of the separator will contact the surface of the fluid sample. At this point, air trapped within the hollow interior of the separator can impede further downward movement of the separator into the fluid sample. However, this air can pass through the defect in the bellows caused by the needle or through some other manufactured defect in the bellows.

The ballast will cause the separator to sink into the fluid sample while the float will buoyantly remain near the surface of the fluid sample thereby causing an elongation and narrowing of the bellows. The less dense liquid phase of the fluid sample will move through the space between the separator and the walls of the tube. As noted above, the overall density of the separator is selected to be less than the density of the formed phase of the fluid sample, but greater than the density of the less dense liquid phase of the fluid sample. Thus, the separator will stabilize at a location between the formed and liquid phases of the fluid sample after a sufficient period of centrifugation. The centrifuge then is stopped. The termination of the centrifugal load enables the toroidal sealing section of the bellows to return to its unbiased dimensions, and into sealing engagement with the interior of the tube. The less dense liquid phase of the fluid sample can be separated from the tube by either removing the closure or passing a needle through the closure. Alternatively, in certain embodiments, the more dense formed phase can be accessed through a sealed opening in the bottom end of the tube.

The separator of the invention comprises a useful range of parameters and there are two principle driving equations for defining the parameters:

$$\sigma_t V_t = \sigma_f V_f + \sigma_s V_s$$

Conservation of Mass $$((\sigma_f - \sigma_t) V_f - (\sigma_s - \sigma_t) V_s) \rho_w = (\delta \cdot \Delta D \cdot k)/a$$

Force Balance

The following non-dimensional parameters may then be substituted into the force balance:

$$V_s^* = V_s/D^3; V_f^* = V_f/D^3; S^* = k/a\rho_w D^2$$

to arrive at:

$$((\sigma_f - \sigma_t)V_f^* - (\sigma_s - \sigma_t)V_s^*) = (\delta \cdot \Delta D \cdot S^*)/D$$

So as to scale prototypes to any size device, wherein the following are defined:

"$\sigma_t$", "$\sigma_f$", "$\sigma_s$", are the specific gravities of the separator device, float, and ballast, respectively;

"$V_t$", "$V_f$", "$V_s$" are the volumes of the separator device, float, and ballast, respectively;

"$\rho_w$" is the density of water;

"k" is the separator spring constant;

"a" is the applied acceleration; and the deflection ration defined by: $\Delta L/\Delta D$, where "$\Delta L$" is the change in length.

The left side of the equation can be an infinite number of combinations of materials and geometries and if it is equal to the product of the right side it can be concluded that the device will function.

Desirable values for the right side of the equation are as follows:

$\delta = 1.5-3.5$ $\Delta D/D = 0.05$ to $0.2$ $S^* = 0.043$ to $0.220$.

One embodiment of the invention is illustrated in FIGS. 1 and 13-15, wherein assembly 10 includes a tube 12, a closure 14, and a separator assembly 16. Tube 12 includes a closed bottom 18, an open top 20, and a cylindrical sidewall 22 extending therebetween. Sidewall 22 includes an inner surface 23 with an inside diameter "a" extending from top end 20 to a location substantially adjacent bottom end 18.

Figure 1:
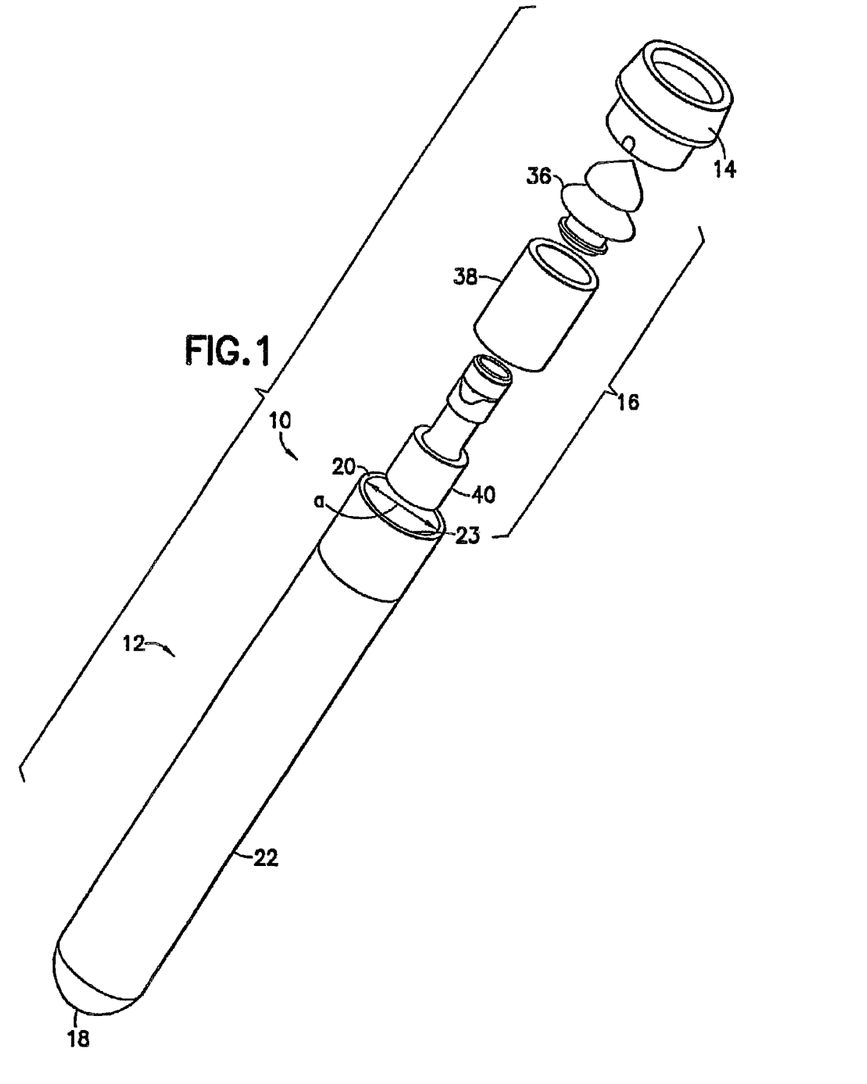
FIG. 1 is an exploded perspective view of an assembly of one embodiment of the invention.
Figure 2:
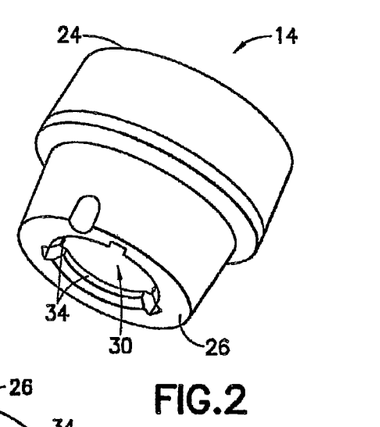
FIG. 2 is a perspective view of the closure of the assembly of FIG. 1.
Figure 3:
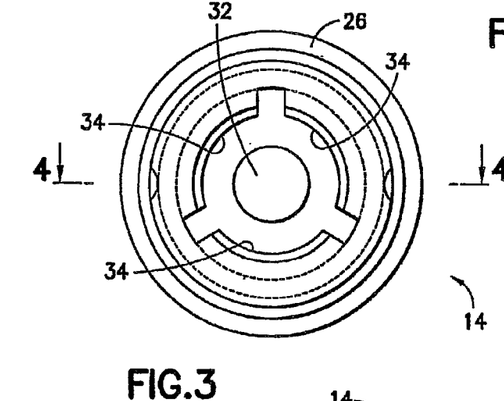
FIG. 3 is a bottom plan view of the closure of FIG. 2.
Figure 4:
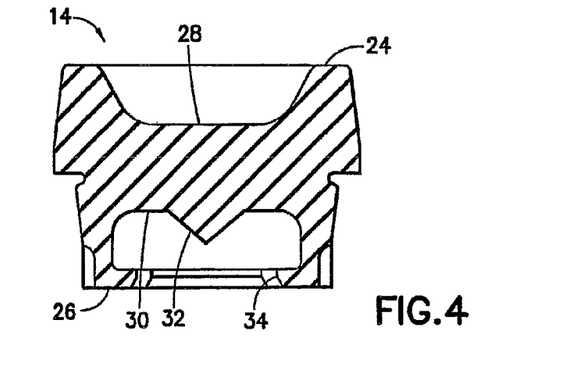
FIG. 4 is a cross-sectional view of the closure of FIG. 3 thereof.

Closure 14, as shown in FIGS. 2-4, is unitarily molded from an elastomeric material and includes a top end 24 and a bottom end 26. Portions of closure 14 adjacent top end 24 define a maximum outside diameter which exceeds the inside diameter "a" of tube 12. Additionally, portions of closure 14 at top end 24 include a central recess 28 which defines a needle pierceable resealable septum. Portions of closure 14 extending upwardly from bottom end 26 taper from a minor diameter which is approximately equal to or slightly less than the inside diameter "a" of tube 12 to a major diameter that is greater than inside diameter "a". Thus, bottom end 26 of closure 14 can be urged into portions of tube 12 adjacent open top end 20 thereof, and the inherent resiliency of closure 14 will ensure a sealing engagement with the inner circumferential surface of cylindrical sidewall 22 of tube 12.

Closure 14 is formed to include a bottom recess 30 extending into bottom end 26. Bottom recess 30 is characterized by a central convex cone 32. Additionally, a plurality of spaced apart resiliently deflectable arcuate flanges 34 extend around the entrance to recess 30. Flanges 34 function to releasably hold separator assembly 16.

Figure 5:
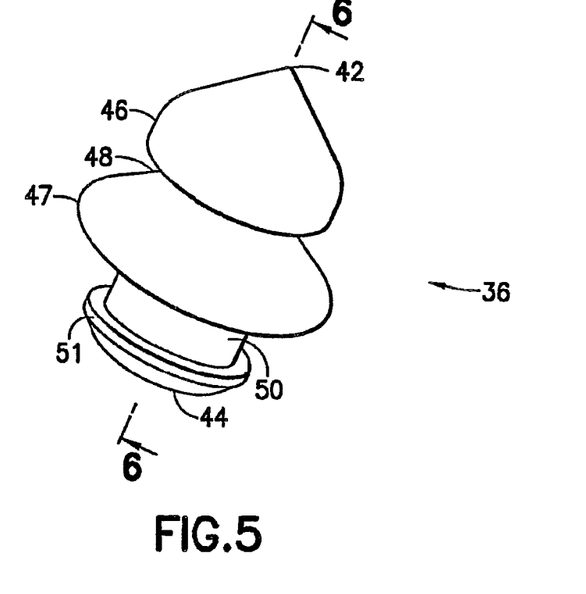
FIG. 5 is a perspective view of the bellows of the separator of the assembly of FIG. 1.
Figure 6:
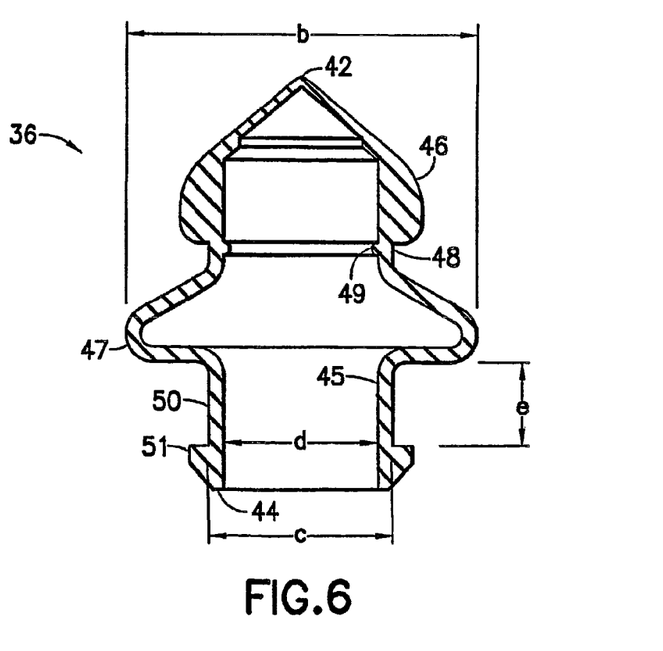
FIG. 6 is a cross-sectional view of the bellows of FIG. 5 taken along line 6-6 thereof.

Separator assembly 16 includes a bellows 36, a ballast 38, and a float 40. Bellows 36, as shown in FIGS. 5 and 6, is unitarily molded from a resiliently deformable material, that exhibits good sealing characteristics. More particularly, bellows 36 is symmetrical about a center axis and includes an upper end 42, a lower end 44, and a hollow interior 45 that is open at lower end 44. Portions of bellows 36 adjacent upper end 42 define an enlarged mounting head 46 with a top section that is convexly conical in an initial unbiased condition of bellows 36. The conical section of bellows 36 adjacent upper end 42 can be deflected into a conical concave configuration that abuts conical portion 32 in recess 30 of closure 14. Bellows 36 further includes a generally toroidal sealing section 47 with intermediate upper and lower ends 42 and 44. Toroidal sealing section 47 defines an outside diameter "b" which, in an unbiased condition of bellows 36, slightly exceeds inside diameter "a" of tube 12. However, oppositely directed forces on upper and lower ends 42 and 44 of bellows 36 will lengthen bellows 36 simultaneously reducing the diameter of toroidal sealing section 47 to a dimension less than "a". A narrow neck 48 is defined between mounting head 46 and toroidal sealing section 47. Neck 48 is dimensioned to be engaged within the area defined by arcuate flanges 34 on closure 14. Hollow interior 45 of bellows 36 includes an annular float mounting bead 49 at a location substantially aligned with neck 48.

Portions of bellows 36 between toroidal sealing section 47 and lower end 44 define a generally cylindrical ballast mounting section 50 of outside diameter "c", inside diameter "d," and length "e". Ballast mounting section 50 terminates at an outwardly projecting flange 51 substantially adjacent lower end 44 of bellows 36.

Figure 7:
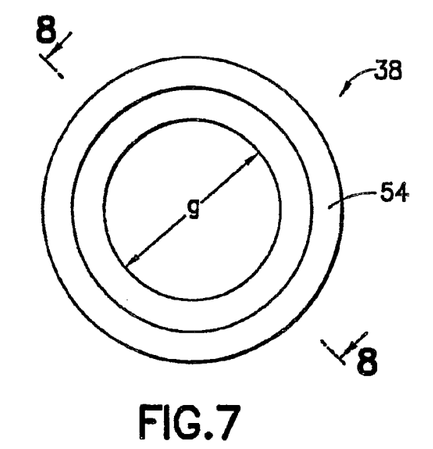
FIG. 7 is a bottom plan view of the ballast of the separator of the assembly of FIG. 1.
Figure 8:
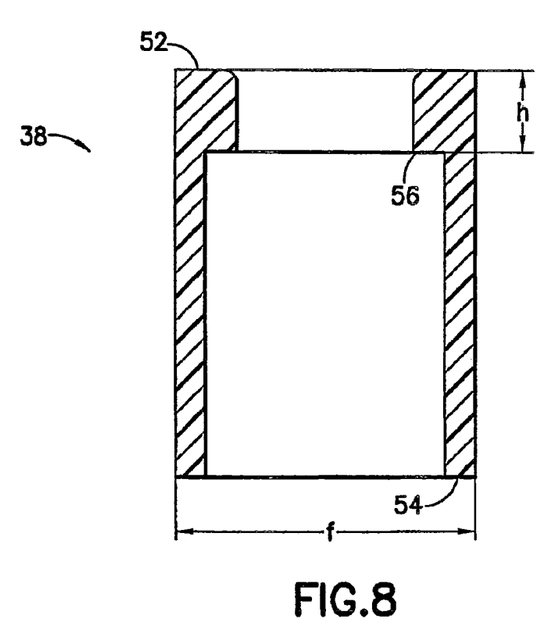
FIG. 8 is a cross-sectional view of the ballast of FIG. 7 taken along line 8-8 thereof.

Ballast 38 of separator 16 is generally a cylindrical tube unitarily formed from a material that will not react with blood or other liquid being separated and that has a density higher than the blood or other liquid being separated. Ballast 38 preferably is substantially tubular and includes opposed upper and lower ends 52 and 54, as shown in FIGS. 7 and 8. Outer circumferential surface areas of ballast 38 define a maximum outside diameter "f" that is less than inside diameter "a" of tube 12. Inner circumferential surface regions of ballast 38 are characterized by an inwardly directed flange 56 adjacent upper end 52. Flange 56 defines an inside diameter "g" which is approximately equal to outside diameter "c" of ballast mounting section 50 of bellows 36. Additionally, flange 56 of ballast 38 defines a length "h" which is approximately equal to length "e" of ballast mounting section 50 on bellows 36. As a result, ballast 38 can be securely mounted to ballast mounting section 50 of bellows 36 at locations between flange 51 and toroidal sealing section 47. Portions of ballast 38 between flange 56 and lower end 54 of ballast 38 will project downwardly below lower end 44 of bellows 36 in this interengaged position.

Figure 9:
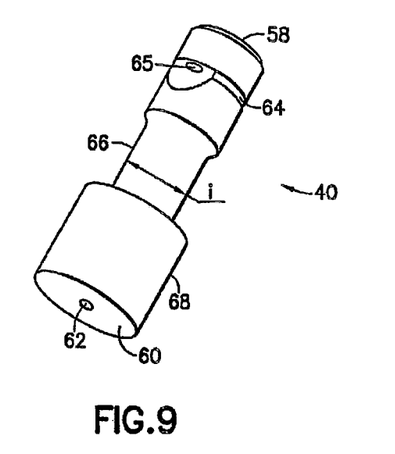
FIG. 9 is a perspective view of the float of the separator of the assembly of FIG. 1.
Figure 10:
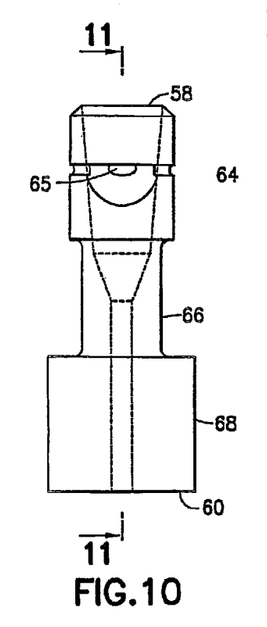
FIG. 10 is a side elevational view of the float of the separator of the assembly of FIG. 1.
Figure 11:
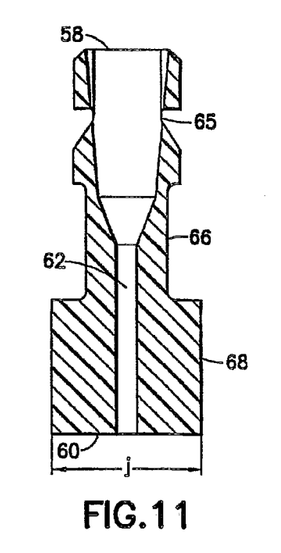
FIG. 11 is a cross-sectional view of the float of FIG. 10 taken along line 11-11 thereof.

Float 40 of separator 16 is a generally stepped tubular structure unitarily molded from a foam material having a density less than the density of the liquid phase of blood. Float 40 may be unitarily formed from a low density polyethylene. As shown in FIGS. 9-11, float 40 has an upper end 58, a lower end 60, and a passage 62 extending axially therebetween. Float 40 is formed with an annular groove 64 extending around the outer circumferential surface thereof at a location spaced slightly from upper end 58. Annular groove 64 is dimensioned to be resiliently engaged by inwardly directed annular bead 49 of bellows 36 for securely retaining portions of float 40 near upper end 58 to portions of bellows 36 near lower end 44 thereof. Additionally, groove 64 is configured to define apertures 65 that enable an air flow that insures narrowing of bellows 36 in the assembled condition of separator 16, as explained below.

Float 40 further includes narrow neck 66 at locations approximately midway between top and bottom ends 58 and 60. Neck 66 defines a diameter "i" which is less than inside diameter "d" of ballast mounting section 50 of bellows 36. As a result, neck 66 is freely movable in an axial direction within ballast mounting section 50 of bellows 36.

Float 40 further includes a substantially cylindrical base 68 defining a diameter "j" which is less than the inside diameter of ballast 38 between flange 56 and lower end 54. Thus, base 68 of float 40 can be slidably moved in an axial direction relative to portions of ballast 38 adjacent bottom end 54 thereof.

Separator 16 is assembled by resiliently engaging ballast mounting section 50 of bellows 36 with flange 56 of ballast 38. Float 40 then is urged upwardly through ballast 38 and into lower end 44 of bellows 36. After sufficient insertion, annular groove 64 of float 40 will engage annular bead 49 of bellows 36. Thus, bellows 36, ballast 38, and float 40 will be securely engaged with one another.

Portions of separator 16 adjacent upper end 42 of bellows 36 then are urged into recess 30 in bottom end 26 of closure 14. This insertion will cause arcuate flanges 34 of closure 14 to deflect. After sufficient insertion, arcuate flanges 34 will resiliently return toward an undeflected condition in which flanges 34 engage neck 48 of bellows 36. Additionally, the concave cone at upper end 42 of bellows 36 is deflected downwardly and into a convex shape by cone 32 of closure 14.

Figure 12:
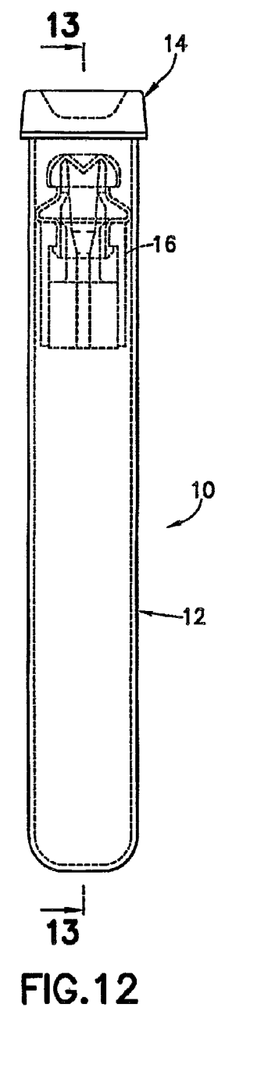
FIG. 12 is a side elevational view of an assembly of an embodiment of the invention.
Figure 13:
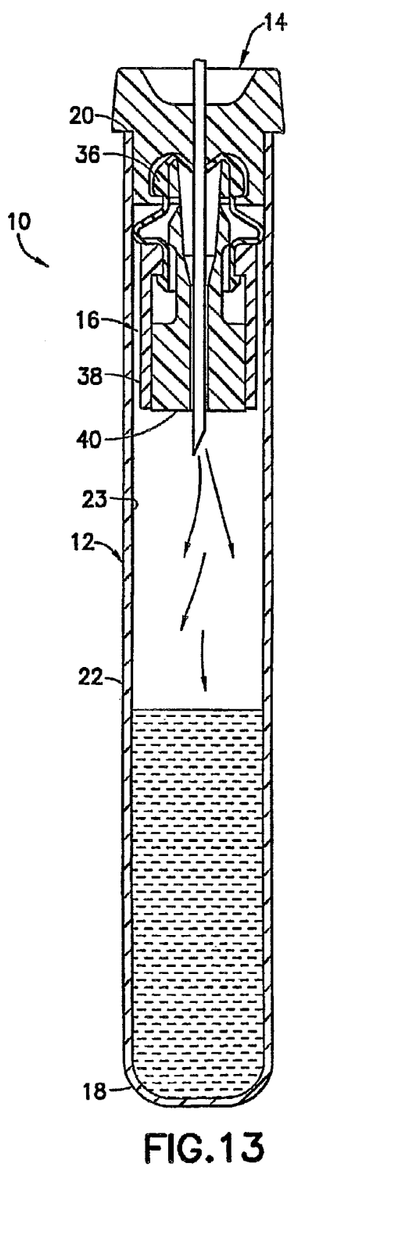
FIG. 13 is a cross-sectional view of the assembly of FIG. 12 taken along line 13-13 thereof.

The subassembly comprised of closure 14 and separator 16 then is inserted into open top 20 of tube 12 such that separator 16 and lower end 26 of closure 14 lie within tube 12, as shown in FIGS. 12 and 13. Closure 14 will sealingly engage against interior surface regions and top end 20 of tube 12. Additionally, toroidal section 48 of bellows 36 will sealingly engage against inner surface 23 of tube 12.

As shown in FIG. 13, a liquid sample is delivered to the tube by a needle that penetrates septum 28 of closure 14 and upper end 42 of bellows 36. For purposes of illustration only, the liquid sample is blood. Blood will flow through central opening 62 of float 40 and to bottom end 18 of tube 12. The needle then will be withdrawn from assembly 10. Upon removal of the needle septum 28, closure 14 will reseal itself. Upper end 42 of bellows 36 also will reclose itself in a manner that will render it substantially impervious to fluid flow.

Figure 14:
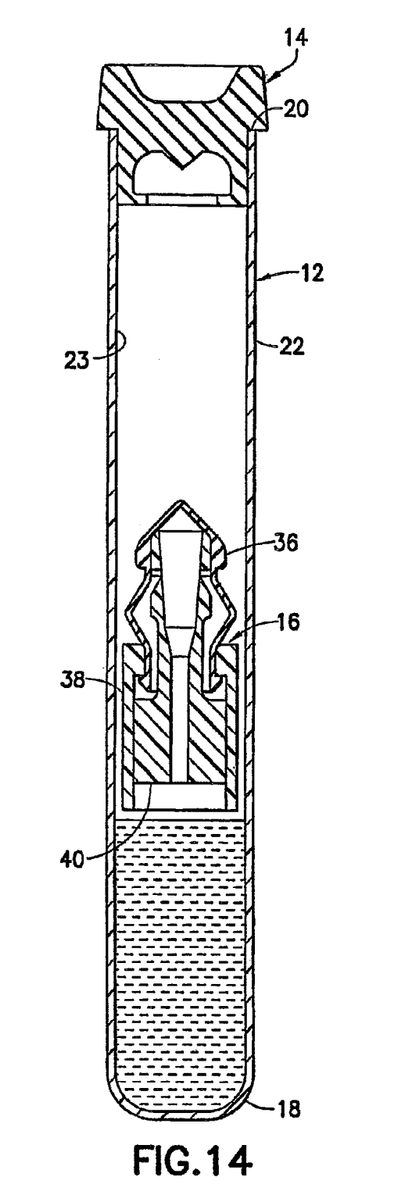
FIG. 14 is a cross-sectional view of the assembly of FIG. 12 taken along line 13-13 thereof, showing the separator under a centrifugal load.
Figure 15:
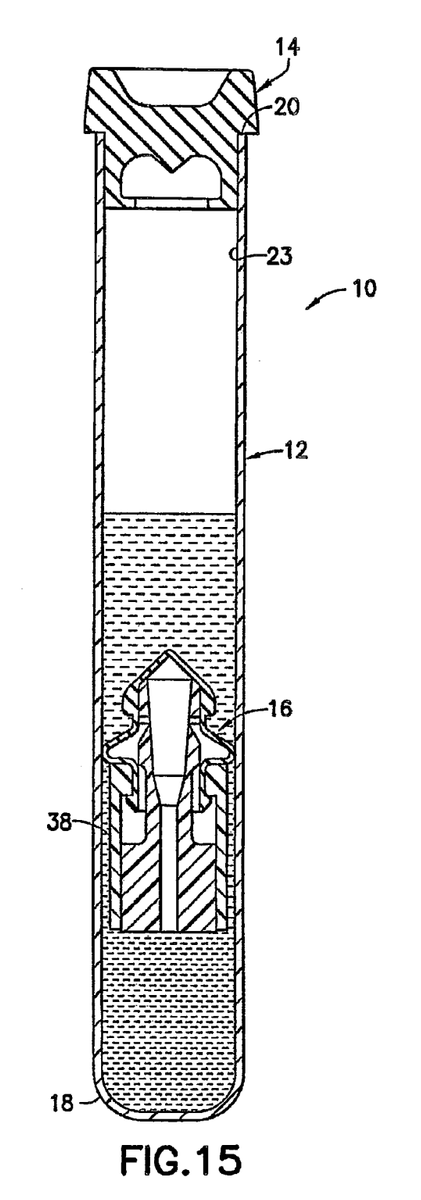
FIG. 15 is a cross-sectional view of the assembly of FIG. 12 taken along line 13-13 thereof, showing the separator sealingly engaged with the tube between the liquid and formed phases of the fluid sample.

As shown in FIG. 14, when assembly 10 is subjected to centrifugation or to an axial centrifugation force, the respective phases of the blood will begin to separate so that the more dense phase comprising red blood cells will be displaced toward the bottom end 18 of tube 12 and so that the less dense phase comprising serum or plasma will be displaced to a location immediately above the denser phase. Simultaneously, the centrifugal loads will urge ballast 38 toward bottom end 18 of tube 12 relative to float 40. This movement of ballast 38 will generate a longitudinal deformation of bellows 36. As a result, toroidal sealing section 48 will become longer and narrower and will be spaced concentrically inwardly from the inner surface 23 of sidewall 20 of tube 12. The smaller cross-section of toroidal section 48 will permit a movement of portions of bellows 36 adjacent lower end 44 to move toward bottom 18 of tube 12. Upper end 42 of bellows 36 initially will be retained adjacent closure 14 by arcuate flanges 34. However, all of closure 14 is resiliently deformable, and hence arcuate flanges 34 will resiliently deform downwardly in response to centrifugal loads created on separator 16, and particularly on ballast 38. Hence, separator 16 will separate from closure 14 and will begin moving in tube 12 toward bottom end 18, as shown in FIG. 14. Air in portions of tube 12 between the blood and separator 16 will flow around separator 16 and into sections of tube 12 between separator 16 and closure 14. After sufficient movement of separator 16, bottom end 54 of ballast 38 and/or bottom end 60 of float 40 will contact the top surface of the blood. This will leave trapped air within aperture 62 of float 40 that could impede further downward movement of separator 16. However, the defect in top 42 of bellows 36 caused by the needle cannula will enable trapped air to escape to regions of tube 12 between separator 16 and closure 14. Thus, ballast 38 will continue to urge separator 16 down into the separating blood with a liquid phase capable of moving around and above the separator. As noted above, separator 16 has an overall density between the densities of the formed and liquid phases of the blood. Consequently, separator 16 will stabilize in a position within tube 12 such that the formed phase of the blood will lie between bottom end 18 of tube 12 and separator 16, as shown in FIG. 15. The liquid phases of the blood will lie between separator 16 and closure 14.

After this stabilized state has been reached, the centrifuge will be stopped. The termination of the centrifugal load will cause toroidal sealing section 48 of bellows 36 to resiliently return toward its unbiased condition and into sealing engagement with interior surface 23 of tube 12. Thus, the formed and liquid phases of blood will be separated efficiently and can be accessed separately for analysis.

Figure 16:
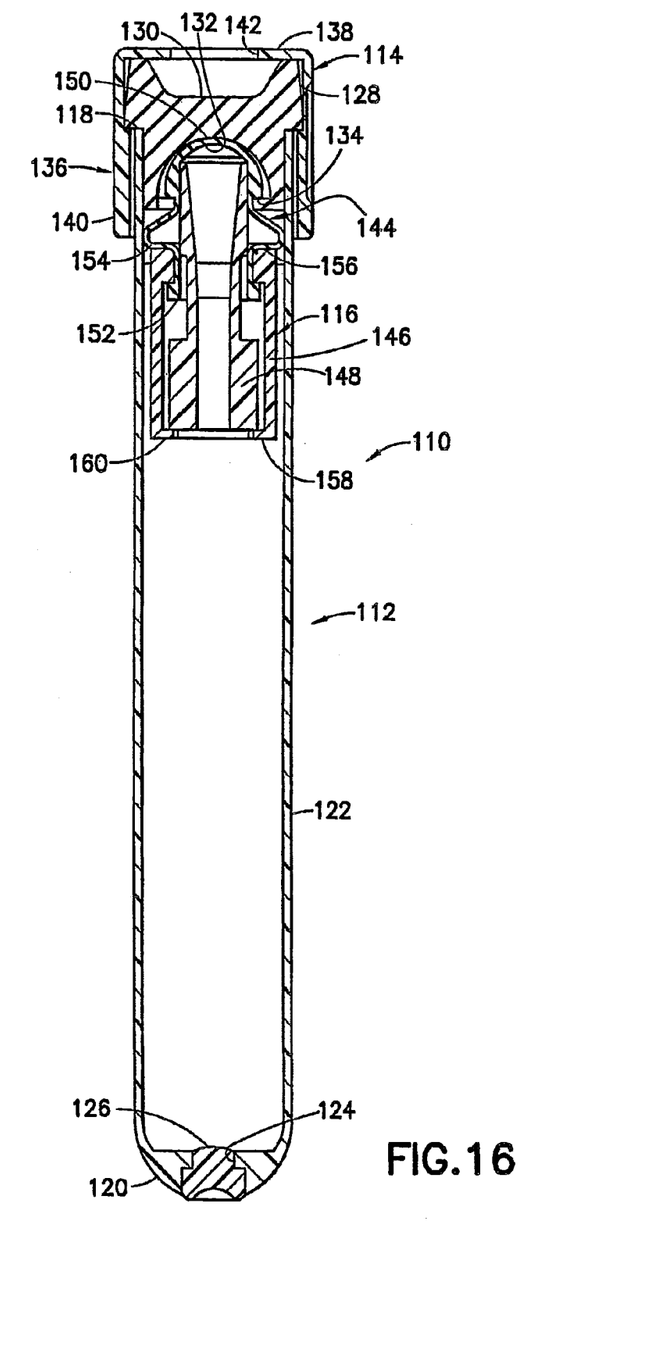
FIG. 16 is a cross-sectional view similar to FIG. 13, but showing an alternate embodiment of the invention.

An alternate embodiment of the tube assembly in accordance with the subject invention is identified generally by the numeral 110 in FIG. 16. Assembly 110 includes a tube 112, a closure 114, and a separator 116.

Tube 112 includes an open top 118, a bottom 120, and a cylindrical wall 122 extending therebetween. Bottom 120 of tube 112 has an opening 124 extending therethrough. A bottom closure 126 is sealingly engaged in opening 124. Bottom closure 126 is formed from a needle pierceable elastomer and enables the formed phase of a blood sample to be accessed directly from bottom 120 of tube 112.

Closure 114 includes an elastomeric stopper 128 sealingly engaged in open top 118 of tube 112. Stopper 128 is provided with a centrally disposed needle pierceable septum 130. Stopper 128 further includes a bottom recess 132 having a plurality of inwardly directed resiliently deflectable arcuate flanges 134 extending thereabout.

Closure 114 further includes an outer cap 136 having an annular top wall 138 and a generally cylindrical skirt 140 depending downwardly from top wall 138. Cap 136 is securely mounted around stopper 128 and is removably mountable over open top 118 of tube 112. Top wall 138 of cap 136 is provided with a central opening 142 that substantially registers with septum 130.

Separator 116 includes a bellows 144, a ballast 146, and a float 148. Bellows 144 includes an upper end 150, a lower end 152, and a toroidal sealing 154 therebetween. Unlike the prior embodiment, portions of bellows 144 adjacent upper end 150 are not conically generated. Rather, these upper portions of bellows 144 are substantially spherically generated and will nest with recess 132 in stopper 128 without the inward deformation that had been described with respect to the first embodiment. Portions of bellows 144 adjacent lower end 152 and adjacent toroidal sealing 154 are substantially the same as in the prior embodiment.

Ballast 146 includes an upper end 156 and a lower end 158. Portions of ballast 146 in proximity to lower end 158 defer from the prior embodiment in that inwardly directed flanges 160 are provided for trapping float 148. Thus, any post-assembly downward movement of float 148 relative to ballast 146 is substantially prevented. However, upward movement of float 148 relative to ballast 146 is possible, and will occur during centrifugation.

Alternatively, it is possible for the separator element to be a unitary structure having regions of varying densities that provide the functionality of the buoyancy member and ballast member.

Figure 17:
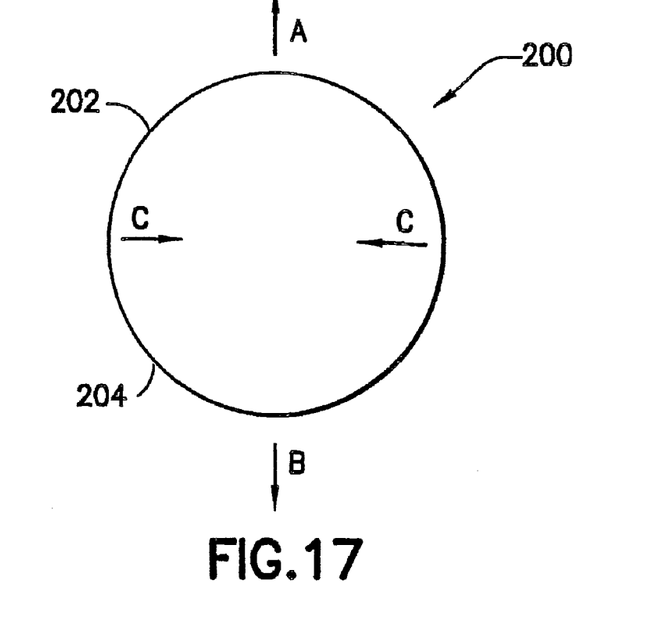
FIG. 17 illustrates a further embodiment of the invention.

In one such embodiment, reflected in FIG. 17, the separator element 200 is a unitary element formed from a polymeric material, where the upper region 202 of the element comprises a lower-density material, and the lower region 204 contains a higher density material. Upon centrifugation, the lower and higher density regions would act as the buoyancy and ballast members, respectively. The middle region is not required to contribute to buoyancy or ballast, and may be equivalent to the overall density of the device. The separator element 200 may be spherical in shape, but variations are possible to optimize the sealing and movement of the separator for its intended application.

There are numerous molding techniques for fabricating such a separator. The equations and relationships disclosed herein can be used to determine a desired density distribution, and the various molding processes available can be adjusted accordingly.

In one technique, it is possible to mold a body from a single material, but with gas bubbles, either many small bubbles or one or a few large bubbles, dispersed in the upper region to provide a lowered density relative to the remainder of the separator. This could be done for example by use of a supercooled or supercritical fluid injected into the polymer material. One commercial technique for doing so is the MuCell® process owned by Trexel, Inc., Woburn, Mass., and reflected in U.S. Pat. Nos. 5,158,986, RE37,932, and 5,160,674, the disclosures of which are hereby incorporated by reference. Other conventional foaming techniques may also be used selectively during injection molding to provide a desired density.

Figure 18:
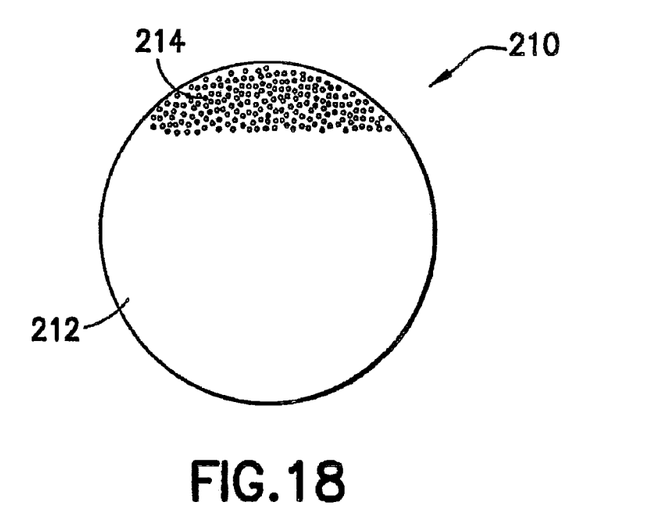
FIG. 18 illustrates another embodiment of the invention.

In another technique, it is possible to add higher density additives to a lower region of a single material matrix, or to add lower density additives to an upper region of a single material matrix. For example, it is possible to perform injection molding with introduction of an additive (e.g., a low or high density additive) to provide a desired density gradient. As shown in the cross-section view of FIG. 18, this could be used to provide a separator 210 having a high density matrix 212 with low density additive 214 at an upper region thereof. This approach could also provide a low density matrix with high density components at a lower region thereof, or a matrix with high density additives at one region and low density additives at another region. The matrix may have a concentration gradient of the additive to provide a desirable density distribution, or may have isolated regions with additive present therein. Examples of suitable additives include solid or hollow beads such as glass beads, as well as hollow or solid fibers, and clay composites.

The separator may also be formed from two or more materials, e.g., compatible materials having different densities, by a technique such as two-shot molding (which can be more than two shots), or by co-injection molding. The separator may also be formed from the same material with differing molding parameters to provide differing densities, for example selective use of a process such as MuCell® or other selective incorporation of the additives noted above, or selective use of molding temperatures. Other processes that may be suitable include gas-assist, overmolding, and co-injection plus MuCell®.

The unitary separator is formed of any suitable materials that provide the needed density and elastomeric properties, are capable of being used with the techniques needed to form the unitary separator, and that are inert with respect to the collected sample. One suitable material would be the Kraton™ family of materials (block copolymers of styrene and rubber); soft silicones are also possible.

As discussed above, it is generally desirable to direct blood into the container such that the blood is able to get beneath the separator, since serum tubes for some applications require the red blood cells to be below the separator (e.g., where the red blood cells clot and are to be separated from the serum). (This is less important for plasma tubes.) Such an outcome is difficult if the separator starts on the bottom of the tube. There are at least two solutions to this problem. One is to design the separator to be secured at the top of the blood collection tube, such that the non-patient end of the needle can be inserted through the separator into the tube interior. The separator would thus be formed of a material pierceable by such a needle, and of a size/shape to allow the needle to pass completely through. The shape of the separator would be designed accordingly, and thus might incorporate for example a divot or recess at its lower end to allow access through the separator into the reservoir portion of the tube. Securement of the separator at the top end of the tube could be attained by molding in a feature that mates with a corresponding feature of the tube closure, or by utilizing a tube taper that holds the separator at the top of the tube prior to centrifugation.

An alternative is to form a tube with openings (and stoppers) on both ends. The separator is inserted proximate the stopper at one end, and the blood is directed into the tube via the opposite stopper. For plasma separation tubes where an anticoagulant is present, the separator can be placed at the bottom of the tube initially, and blood can be directed onto it, without detrimental effects.

The separator would function essentially in the same manner as the multi-component separator discussed above. Specifically, upon centrifugation and immersion of the separator in the fluid, as reflected by the arrows A and B in FIG. 17, the lower density upper region 202 provides a buoyant upward force on the separator relative to the fluid. Simultaneously, the higher density lower region 204 provides an axial force downward on the separator. The combined forces stretch and elongate a middle region 203 of the separator axially, shown by arrows C, causing inward radial movement of the middle region. This radial movement pulls the separator out of contact with the inner wall of the tube so that it is free to move axially without any frictional drag. (Note that the middle region may have the same density as the upper or the lower region, but provides the sealing function due to its location in the middle portion of the separator.)

Therefore, a path is developed between the inner wall of the tube and the separator that permits the flow of the low-density blood component past the separator as it migrates down the tube. Migration of the separator terminates when it reaches the position between the lower density fluid component and higher density fluid or cellular/solid components, equal to its overall density. Upon terminating centrifugation, the separator expands to its undeformed shape, sealing against the inner wall of the tube, thereby creating a barrier between the higher and lower density components of the sample fluid.

Other embodiments of the invention will be apparent from the disclosure herein.

What is claimed is:

1. A method for manufacturing a biological fluid collection container having therein a separator for separating components of a collected fluid sample, the method comprising:
    providing the biological fluid collection container; and
    placing the separator into the container, wherein the separator is manufactured by a method comprising the step of injecting one or more polymers into a mold to form a unitary component comprising at least one feature selected from the group consisting of at least two regions of differing densities and a density gradient, wherein at least a portion of the separator is adapted to deform upon application of rotational force.

2. The method of claim 1, wherein the injecting step further comprises the step of providing one or more additives in at least one of the polymers.

3. The method of claim 2, wherein the one or more additives are selected from the group consisting of beads and fibers.

4. The method of claim 3, wherein the one or more additives comprise hollow glass beads.

5. The method of claim 1, wherein the injecting step further comprises the step of providing voids or bubbles in at least one of the polymers.

6. The method of claim 5, wherein the voids or bubbles are provided by injecting a supercritical or supercooled fluid into at least one of the polymers.

7. The method of claim 1, wherein the injecting step comprises injecting at least two polymers with differing densities.

8. The method of claim 1, wherein the injecting step comprises injecting a single polymer such that the density of the polymer is varied during the injection.

9. The method of claim 1, wherein the injecting step comprises at least one molding process selected from the group consisting of two-shot, overmolding, and co-injection.

\* \* \* \* \*